US011472705B2

(12) United States Patent
Regev et al.

(10) Patent No.: US 11,472,705 B2
(45) Date of Patent: Oct. 18, 2022

(54) NITRIC OXIDE RELEASING COMPOSITIONS

(71) Applicant: SaNOtize Research and Development Corp., Vancouver (CA)

(72) Inventors: Gilly Regev, Vancouver (CA); Christopher C. Miller, North Vancouver (CA)

(73) Assignee: SaNOtize Research and Development Corp., Vancouver (CA)

( * ) Notice: Subject to any disclaimer, the term of this patent is extended or adjusted under 35 U.S.C. 154(b) by 292 days.

(21) Appl. No.: 16/352,741

(22) Filed: Mar. 13, 2019

(65) Prior Publication Data

US 2019/0367366 A1 Dec. 5, 2019

Related U.S. Application Data

(60) Provisional application No. 62/642,536, filed on Mar. 13, 2018.

(51) Int. Cl.
*C01B 21/24* (2006.01)
*A61K 47/02* (2006.01)
*A61K 47/12* (2006.01)

(52) U.S. Cl.
CPC ............ *C01B 21/24* (2013.01); *A61K 47/02* (2013.01); *A61K 47/12* (2013.01); *C01P 2006/12* (2013.01); *C01P 2006/14* (2013.01)

(58) Field of Classification Search
None
See application file for complete search history.

(56) References Cited

U.S. PATENT DOCUMENTS

| 6,605,304 | B1 * | 8/2003 | Wellinghoff ......... C11D 3/0052 424/489 |
| 6,709,681 | B2 | 3/2004 | Benjamin et al. |
| 7,040,313 | B2 | 5/2006 | Fine et al. |
| 7,048,951 | B1 | 5/2006 | Seitz et al. |
| 8,980,331 | B2 | 3/2015 | Chen et al. |
| 9,445,996 | B2 | 9/2016 | Chen et al. |
| 10,537,697 | B2 | 1/2020 | Montgomery et al. |
| 10,543,336 | B2 | 1/2020 | Miller et al. |
| 10,758,703 | B2 | 1/2020 | Kohlmann et al. |
| 10,751,364 | B2 | 8/2020 | Miller et al. |
| 11,304,972 | B2 | 4/2022 | Miller et al. |
| 2005/0036949 | A1 | 2/2005 | Tucker et al. |
| 2005/0037093 | A1 | 2/2005 | Benjamin |
| 2006/0008529 | A1 | 1/2006 | Meyerhoff et al. |
| 2007/0116785 | A1 | 5/2007 | Miller |
| 2009/0196930 | A1 | 8/2009 | Surber et al. |
| 2010/0040703 | A1 | 2/2010 | Miller et al. |
| 2010/0262095 | A1 | 10/2010 | Hall |
| 2012/0003293 | A1 | 1/2012 | Miller et al. |
| 2013/0330244 | A1 | 12/2013 | Balaban et al. |
| 2014/0056963 | A1 * | 2/2014 | Chen ........................ A61K 9/14 424/445 |
| 2015/0030702 | A1 * | 1/2015 | Jezek .................. A61L 26/0066 424/666 |
| 2015/0157657 | A1 | 6/2015 | Stenzler et al. |
| 2021/0038838 | A1 | 2/2021 | Acker et al. |
| 2021/0145732 | A1 | 5/2021 | Minton et al. |
| 2022/0040224 | A1 | 2/2022 | Miller et al. |
| 2022/0088342 | A1 | 3/2022 | Fine |
| 2022/0160792 | A1 | 5/2022 | Bryan |

FOREIGN PATENT DOCUMENTS

| CA | 2930189 A1 | 4/2015 |
| CA | 2946828 A1 | 9/2015 |
| CA | 2706828 C | 12/2016 |
| WO | WO 9939574 A2 | 8/1999 |
| WO | WO 2003013489 A1 | 2/2003 |
| WO | WO 2003020211 A2 | 3/2003 |
| WO | WO 2009019498 A2 | 2/2009 |
| WO | WO 2009086470 A2 | 7/2009 |
| WO | WO 2009097343 A1 | 8/2009 |
| WO | WO 2009131931 A1 | 10/2009 |
| WO | WO 2011085484 A1 | 7/2011 |
| WO | WO 2013063354 A1 | 5/2013 |
| WO | WO 2015058127 A1 | 4/2015 |
| WO | WO 2015138406 A1 | 9/2015 |
| WO | WO 2018/049291 | 3/2018 |

OTHER PUBLICATIONS

Gregg et al.; "Functionalised Solids Delivering Bioactive Nitric Oxide Gas for Therapeutic Applications;" Materials Today Communications; (2017); pp. 95-105; vol. 12; <doi: 10.1016/j.mtcomm.2017.07.007 >.
Schairer et al.; "The Potential of Nitric Oxide Releasing Therapies as Antimicrobial Agents;" Virulence; (May/Jun. 2012); pp. 271-279; vol. 3, No. 3; <doi: 10.4161/viru.20328 >.
Seabra et al.; "Nictric Oxide-Releasing Vehicles for Biomedical Applications;" Journal of Materials Chemistry; (2010); pp. 1624-1637; vol. 20; <doi: 10.1039/b912493b >.
International Search Report dated Sep. 11, 2019, in International Application No. PCT/IB2019/000472, filed Mar. 13, 2019; 7 pages.
Adam et al.; "A Clinical Trial of Hypertonic Saline Nasal Spray in Subjects with the Common Cold or Rhinosinusitis;" Archives of Family Medicine; (Jan.-Feb. 1998); pp. 39-43; vol. 7, No. 1.
Meinert et al.; "Clinical Trials: Design, Conduct, and Analysis;" Monographs in Epidemiology and Biostatistics; (1986); 11 pages; vol. 8; [Contents].

(Continued)

*Primary Examiner* — Joseph D Anthony
(74) *Attorney, Agent, or Firm* — Thorpe North & Western, LLP; David W. Osborne

(57) ABSTRACT

Nitric oxide (NO) generating compositions can include a nitrite component, an acidifying component, and a support material configured to carry one of the nitrite component and the acidifying agent. In some examples, the support material can minimize NO generation prior to addition of an activating amount of a suitable solvent.

11 Claims, No Drawings

(56) References Cited

OTHER PUBLICATIONS

Regev-Shoshani et al.: "Prophylactic Nitric Oxide Treatment Reduces Incidence of Bovine Respiratory Disease Complex in Beef Cattle Arriving at a Feedlot;" Research in Veterinary Science; (Oct. 2014); pp. 606-611; vol. 95, No. 2.
Regev-Shoshani et al.; "A Nitric Oxide-Releasing Solution as a Potential Treatment for Fungi Associated with Tinea Pedis;" Journal of Applied Microbiology; (Feb. 2013); pp. 536-544; vol. 114, No. 2.
Regev-Shoshani et al.; "Safety, Bioavailability and Mechanism of Action of Nitric Oxide to Control Bovine Respiratory Disease Complex in Calves Entering a Feetlot;" Research in Veterinary Science; (Apr. 2014); pp. 328-337; vol. 96, No. 2.
Taylor et al.; "Early Results Using a Dynamic Method for Delayed Primary Closure of Fasciotomy Wounds;" Journal of American College of Surgeons; (Nov. 2003); pp. 872-878; vol. 197, No. 5.
Weller et al.; "The Effects of Topical Treatment with Acidified Nitrite on Wound Healing in Normal and Diabetic Mice;" Nitric Oxide; (Apr. 27, 2006); pp. 395-399; vol. 15, No. 4; <doi: 10.1016/j.niox.2006.04.002 >.

\* cited by examiner

NITRIC OXIDE RELEASING COMPOSITIONS

PRIORITY DATA

This application claims the benefit of U.S. Provisional Patent Application Ser. No. 62/642,536, filed on Mar. 13, 2018, which is incorporated herein by reference.

BACKGROUND

Nitric Oxide (NO) is a small, unstable diatomic molecule. It measures about 115 picometers in its bond length, and is soluble in hydrophilic and hydrophobic environments. It has free radical like nature, a short half-life, and it is easily oxidized into nitrogen dioxide. Within the body, nitric oxide can be endogenously produced by nitric oxide synthase enzymes (NOS), and is known to be involved in many physiological and pathological processes. For example, a low level of NO in the blood encourages vasodilation to prevent ischemic damage, helps wound healing, and is an effective antimicrobial agent. Conversely, a high level of NO in the blood leads to tissue toxicity and contributes to inflammatory conditions like septic shock, diabetes, and arthritis.

DESCRIPTION OF EMBODIMENTS

Although the following detailed description contains many specifics for the purpose of illustration, a person of ordinary skill in the art will appreciate that many variations and alterations to the following details can be made and are considered to be included herein. As such, the following embodiments are set forth without any loss of generality to, and without imposing limitations upon, any claims set forth. It is also to be understood that the terminology used herein is for the purpose of describing particular embodiments only, and is not intended to be limiting. Unless defined otherwise, all technical and scientific terms used have the same meaning as commonly understood by one of ordinary skill in the art to which this disclosure belongs.

In this written description, the singular forms "a," "an" and "the" provide express support for plural referents unless the context clearly dictates otherwise. Thus, for example, reference to "a particle" includes a plurality of particles.

In this application, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term, like "comprising" or "including," in this written description it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described as comprising a series of steps, the order of such steps as presented is not necessarily the only order in which such steps may be performed, and certain of the stated steps may possibly be omitted and/or certain other steps not described herein may possibly be added to the method.

Occurrences of the phrase "in one embodiment," or "in one aspect," herein do not necessarily all refer to the same embodiment or aspect.

As used herein, "subject" refers to a mammal that may benefit from the administration of NORS. In one aspect the mammal may be a human.

As used herein, the terms "treat," "treatment," or "treating" when used in conjunction with the administration of NORS, including compositions and dosage forms thereof, refers to administration to subjects who are either asymptomatic or symptomatic. In other words, "treat," "treatment," or "treating" can be to reduce, ameliorate or eliminate symptoms associated with a condition present in a subject, or can be prophylactic, (i.e. to prevent or reduce the occurrence of the symptoms in a subject). Such prophylactic treatment can also be referred to as prevention of the condition.

As used herein, the terms "formulation" and "composition" are used interchangeably and refer to a mixture of two or more compounds, elements, or molecules. In some aspects the terms "formulation" and "composition" may be used to refer to a mixture of one or more active agents with a carrier or other excipients. Compositions can take nearly any physical state, including solid, liquid (i.e. solution), or gas. Furthermore, the term "dosage form" can include one or more formulation(s) or composition(s) provided in a format for administration to a subject. In one example, a composition can be a solution that releases nitric oxide.

A "kit" can mean a package or container that includes a composition or dosage form along with instructions regarding application or administration of the composition or dosage form according to a given regimen or within specified time and amount parameters to treat one or more specific indications. For example, a kit could include a NORS composition in a specific volume or amount along with a set of instructions on appropriate administration of the NORS to a subject in order to treat a given condition (e.g. indication). Instructions may include direction for a single type of administration or indication, or for multiple types of administration or indications. Additionally, the amount and form of the NORS composition in the kit can be suitable for a single administration for treatment of a single indication, multiple administrations creating a regimen for one indication, or single or multiple administrations for multiple indications. For example, a composition or dosage form of a NORS composition can be provided in the kit along with instructions for applying the dosage form in terms of amount and volume that is suitable to treat a plurality of indications, such as skin conditions such as acne, or wound healing, or respiratory therapy, or further yet for improving immunity in the sinus and throat areas.

As used herein "NORS" refers to a nitric oxide (NO) releasing solution, composition or substance. In one aspect, NO released from NORS may be a gas.

As used herein a "therapeutic agent" refers to an agent that can have a beneficial or positive effect on a subject when administered to the subject in an appropriate or effective amount. In one aspect, NO can be a therapeutic agent. In another aspect, therapeutic agents can include non-NORS agents with physiologic activity, such as antibiotics, antihistamines, antivirals, antimicrobials, biological molecules, such as siRNA, cDNA, steroids, vasodilators, vasoconstrictors, analgesics, anti-inflammatories, etc. In some aspects, therapeutic agent can be used interchangeably with "active agent" or "drug".

As used herein, an "effective amount" of an agent is an amount sufficient to accomplish a specified task or function desired of the agent. A "therapeutically effective amount" of a composition, drug, or agent refers to a non-toxic, but sufficient amount of the composition, drug, or agent, to achieve therapeutic results in treating or preventing a condition for which the composition, drug, or agent is known to be effective. It is understood that various biological factors may affect the ability of a substance to perform its intended task. Therefore, an "effective amount" or a "therapeutically effective amount" may be dependent in some instances on such biological factors. Further, while the achievement of therapeutic effects may be measured by a physician, veterinarian, or other qualified medical personnel using evaluations known in the art, it is recognized that individual variation and response to treatments may make the achievement of therapeutic effects a somewhat subjective decision. The determination of an effective amount or therapeutically effective amount is well within the ordinary skill in the art of pharmaceutical sciences and medicine. See, for example, Meiner and Tonascia, "Clinical Trials: Design, Conduct, and Analysis," *Monographs in Epidemiology and Biostatistics,* Vol. 8 (1986).

As used herein, a "dosing regimen" or "regimen" such as "treatment dosing regimen," or a "prophylactic dosing regimen" refers to how, when, how much, and for how long a dose of a composition can or should be administered to a subject in order to achieve an intended treatment or effect.

As used herein, the terms "release" and "release rate" are used interchangeably to refer to the discharge or liberation, or rate thereof, of a substance, including without limitation a therapeutic agent, such as NO, from the dosage form or composition containing the substance. In one example, a therapeutic agent may be released in vitro. In another aspect, a therapeutic agent may be released in vivo.

As used herein, "immediate release" or "instant release" can be used interchangeably and refer to immediate or near immediate (i.e. uninhibited or unrestricted) release of an agent or substance, including a therapeutic agent, such as NO, from a composition or formulation.

As used herein, the term "controlled release" refers to non-immediate release of an agent or substance, including a therapeutic agent, such as NO, from a composition or formulation. Examples of specific types of controlled release include without limitation, extended or sustained release and delayed release. Any number of control mechanisms or components can be used to create a controlled release effect, including formulation ingredients or constituents, formulation properties or states, such as pH, an environment in which the formulation is placed, or a combination of formulation ingredients and an environment in which the formulation is placed. In one example, extended release can include release of a therapeutic agent at a level that is sufficient to provide a therapeutic effect or treatment for a non-immediate specified or intended duration of time.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 ml to about 80 ml" should also be understood to provide support for the range of "50 ml to 80 ml." Furthermore, it is to be understood that in this specification support for actual numerical values is provided even when the term "about" is used therewith. For example, the recitation of "about" 30 should be construed as not only providing support for values a little above and a little below 30, but also for the actual numerical value of 30 as well.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually, and further including decimal or fraction values such as 1.8, 2.3, 3.7, and 4.2.

This same principle applies to ranges reciting only one numerical value as a minimum or a maximum. Furthermore, such an interpretation should apply regardless of the breadth of the range or the characteristics being described.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

Reference in this specification may be made to devices, structures, systems, or methods that provide "improved" performance. It is to be understood that unless otherwise stated, such "improvement" is a measure of a benefit obtained based on a comparison to devices, structures, systems or methods in the prior art. Furthermore, it is to be understood that the degree of improved performance may vary between disclosed embodiments and that no equality or consistency in the amount, degree, or realization of improved performance is to be assumed as universally applicable.

Example Embodiments

An initial overview of invention embodiments is provided below and specific embodiments are then described in further detail. This initial summary is intended to aid readers in understanding the technological concepts more quickly, but is not intended to identify key or essential features thereof, nor is it intended to limit the scope of the claimed subject matter.

Outside of the body nitric oxide (NO) can be produced through various ways. For example, NO can be produced by the catalyzed oxidation of ammonia, the extremely endothermic reaction of nitrogen and oxygen as free gases, and from acidified nitrites. Both the oxidation of ammonia and the reaction of free gas require large amounts of energy, rendering the acidified nitrite reaction the most conducive for use in practice. Production of NO from acidified nitrites can be measured in at least 3 ways. For example, NO production can be measured by means of chemiluminescence, Gas Chromatography-Mass Spectrometry (GC-MS), and/or indirectly through the use of a Griess Reagent and spectrophotometer set to a wavelength of 543 nm. Chemiluminescence is a well-known analytical technique that generally involves the emission of light as a result of a chemical reaction. More specifically, decay of a molecule in an excited state to a lower energy state can cause an emission of light, which can be detected by a chemiluminescence analyzer/detector. As one example, nitric oxide (NO) can react with ozone ($O_3$) to produce excited NO that subsequently decays to a lower energy state and emits electromagnetic radiation that is photoelectrically detectable.

An acidified nitrite solution is based on the following reaction:

$$NO_2^- + H^+ \rightarrow HNO_2 \qquad 1.$$

$$2HNO_2 \rightarrow N_2O_3 + H_2O \rightarrow H_2O + NO + NO_2 \qquad 2a.$$

$$3HNO_2 \leftrightarrows 2NO + NO_3^- + H_2O^+ \qquad 2b.$$

This is also the basis for what can be called a Nitric Oxide Releasing Solution, or NORS. A nitrite containing compound (i.e. nitrite component) like sodium or potassium nitrite, for example, can react with a proton donor. The proton donor can be any kind of acidifying agent to allow the reaction to proceed, but may add undesirable intermediates or by-products depending on which acidifying agent is used. In one specific embodiment, a NO measuring device as recited in Applicant's co-pending United States Provisional Patent Application Ser. No. 62/718,946, filed Aug. 14, 2018, which is incorporated herein by reference, can be used to measure NO release from a composition or device.

Acidified nitrite solutions have antimicrobial properties and can be used to fight various types of infections including fungal infections caused by Tinea pedis (athlete's foot), bacterial infections from Propionibacterium acnes, and various viral infections, for example. The effectiveness of the antimicrobial activity can be dependent on a variety of factors, such as the pH of the solution, the concentration of nitrites available for the reaction, the concentration of acidifying agent to allow the reaction to proceed, and other stabilizing factors. The prospect of a NORS allows for the use of NO in treatments without having to use NO gas from a pressurized canister.

However, it is noted that when the nitrite component and the acidifying agent are mixed together in a suitable reaction environment, such as to prepare a NORS, generation of NO can ensue quickly. However, generation of NO will not continue indefinitely. Thus, in some cases, it can be desirable to delay preparation of the NORS until a time of use, or to within a reasonable period prior to a time of use.

Accordingly, the present disclosure is directed to nitric oxide generating compositions, both in inactive forms and active forms, and associated systems, and methods. As a further note, in the present disclosure, it is noted that when discussing nitric oxide generating compositions, associated systems, and associated methods, each of these discussions can be considered applicable to each of these examples, whether or not they are explicitly discussed in the context of that example. Thus, for example, in discussing details about nitric oxide generating compositions per se, such discussion also refers to the associated systems and methods described herein, and vice versa.

In further detail, the present disclosure describes compositions, such as powder compositions, solid compositions, dry compositions, particulate compositions, or the like, that are in a generally inactive form. By "inactive," it is meant that the composition is in a state and/or form that does not produce nitric oxide, or that minimally produces nitric oxide. The particulate composition, or the like, can include a blend of a nitrite component and an acidifying agent. The particulate composition, or the like, can also include a support material configured to carrier the nitrite component, the acidifying agent, or both. However, in some specific examples, one, but not both, of the nitrite component and the acidifying agent can be carried by the support material.

A variety of nitrite components can be used. Generally, any nitrite containing compound can be used, such as a nitrite salt, a nitrite ester, the like, or a combination thereof. In some specific examples, the nitrite component can include sodium nitrite, potassium nitrite, barium nitrite, calcium nitrite, nitrite orotate, amyl nitrite, magnesium nitrite, other inorganic nitrites, other organic nitrites, the like, or a combination thereof.

The nitrite component can be present in the particulate composition in a variety of amounts, depending on the particular application. In some examples, the nitrite component can be present in the particulate composition in an amount of from about 0.5 wt % to about 99.5 wt %. In some additional examples, the nitrite component can be present in the particulate composition in an amount of from about 25 wt % to about 56 wt %. In yet other examples, the nitrite component can be present in the particulate composition in an amount of from about 13 wt % to about 94 wt %. In some other examples, the nitrite component can be present in the particulate composition in an amount of from about 20 wt % to about 40 wt %. In still other examples, the nitrite component can be present in the particulate composition in an amount of from about 40 wt % to about 60 wt %. In some further examples, the nitrite component can be present in the particulate composition in an amount of from about 60 wt % to about 80 wt %, or from about 80 wt % to about 99.5 wt %.

A variety of acidifying agents can also be used. Generally, any acidifying agent that is suitable to react with the nitrite component without generating undesirable by-products can be used. In some specific examples, the acidifying agent can include an organic acid, such as ascorbic acid, ascorbyl palmitate, salicylic acid, malic acid, lactic acid, citric acid, formic acid, benzoic acid, tartaric acid, the like or a combination thereof. In some additional examples, the acidifying agent can include an inorganic acid, such as hydrochloric acid, sulfuric acid, phosphoric acid, the like, or a combination thereof. In some further examples, the acidifying agent can include a combination of an organic acid and an inorganic acid.

The acidifying agent can be present in the particulate composition in a variety of amounts, depending on the particular application. In some examples, the acidifying agent can be present in the particulate composition in an amount of from about 0.5 wt % to about 99.5wt %. In some additional examples, the acidifying agent can be present in the particulate composition in an amount of from about 26 wt % to about 53 wt %. In yet other examples, the acidifying agent can be present in the particulate composition in an amount of from about 3 wt % to about 67 wt %. In some other examples, the acidifying agent can be present in the particulate composition in an amount of from about 20 wt % to about 40 wt %. In still other examples, the acidifying agent can be present in the particulate composition in an amount of from about 40 wt % to about 60 wt %. In some further examples, the acidifying agent can be present in the particulate composition in an amount of from about 60 wt % to about 80 wt %, or from about 80 wt % to about 99.5 wt %.

The proportion of the nitrite component and the acidifying agent can depend on the particular nitrite component employed, the particular acidifying agent employed, the intended application of the composition, and a variety of other factors. Generally, the ratio can be calculated to provide an activated nitric oxide releasing composition with a suitable pH and a suitable production rate of NO. In some examples, the nitrite component and the acidifying agent can be present in the powder composition in a weight ratio of from about 30:1 to about 1:5. In some other examples, the nitrite component and the acidifying agent can be present in the powder composition in a weight ratio of from about 5:1 to about 1:2.

A variety of support materials can also be used. Generally, the support material can include any suitable material that does not react with the nitrite component, the acidifying agent, or nitric oxide. Further, the support material can be associated with the nitrite component, the acidifying agent, or both, in a manner that minimizes or otherwise arrests (e.g. stops or prevents) reactivity between the nitrite component and the acidifying agent prior to activation. As such, the nitrite component and the acidifying agent can be mixed together without generating NO until an activating solvent is added to the particulate composition to dissociate the support material from one or both of the nitrite component and the acidifying agent. Non-limiting examples of support materials can include carbon materials (e.g carbon black, activated carbon, or the like) a metal oxide (e.g. alumina, zirconia, magnesia, titania, or the like), amorphous or crystalline silica (e.g. fumed silica, silica gel, precipitated silica, precipitated silica gels, silicalite, or the like), a silicate (e.g. magnesium silicate, calcium silicate, thorium silicate, an aluminosilicate, or the like), a metal phosphate (e.g. zirconium phosphate, niobium phosphate, or the like), the like, or a combination thereof.

In some examples, the support material can be a calcined support material. Calcination can be performed to remove surface water, hydroxyl content, etc. In some specific examples calcination can be performed at a temperature greater than or equal to 100° C. In some further examples, the support material can have a surface area of at least 0.1 meters squared per gram ($m^2/g$). In still other examples, the support material can have a surface area of from about 5 $m^2/g$ to about 600 $m^2/g$, or from about 50 $m^2/g$ to about 200 $m^2/g$. In yet other examples, the support material can have a pore volume of at least 0.01 cubic centimeters per gram (cc/g). In still other examples, the support material can have a pore volume of from about 0.1 cc/g to about 10 cc/g, or from about 0.2 cc/g to about 2 cc/g.

In some examples, the support material can be configured to carry the nitrite component. In other examples, the support material can be configured to carry the acidifying agent. In either case, the support material can generally be present in a weight ratio with the nitrite component or the acidifying agent of from about 0.05:1 to about 3:1 support material to acidifying agent or nitrite component. In other examples, the support material can be present at a weight ratio with the nitrite component or the acidifying agent of from about 0.08 to about 1:1, or from about 0.1:1 to about 0.5:1 support material to acidifying agent or nitrite component.

In some additional examples, the particulate composition can further include a gelling agent. The gelling agent can also be present in a powder, particulate, or dry form. Non-limiting examples of gelling agents can include a cellulose derivative (e.g. hydroxyethyl cellulose, carboxymethyl cellulose, methyl cellulose, hydroxypropyl methyl cellulose, ethylcellulose, hydroxylpropyl cellulose, etc.), a carbomer, a poloxamer, acacia, alginic acid, sodium alginate, bentonite, gelatin, pectin, magnesium aluminum silicate, polyvinyl alcohol, tragacanth, xanthan gum, the like, or a combination thereof. Other suitable excipients can also be included as desired, such as a colorant, an effervescent agent, a fragrance, the like, or a combination thereof.

In some further examples, an inactive nitric oxide (NO) generating composition can include a nitrite component and an acidifying component. The acidifying component can include an acidifying agent carried by a support material. The nitrite component and the acidifying component can be mixed together in a dry, particulate, or powder form.

Generally, the inactive NO generating composition can include nitrite components, acidifying agents, and support materials as described above, and in the same amounts and proportions. In this particular example, the acidifying agent is carried by the support material, whereas the nitrite component is not. The acidifying agent carried by the support material can be referred to as the acidifying component.

The acidifying component can be included in the inactive NO generating composition in a variety of amounts. In some specific examples, the acidifying component can be included in the inactive NO generating composition in an amount from about 0.5 wt % to about 99.5 wt %. In other examples, the acidifying component can be included in the inactive NO generating composition in an amount from about 45 wt % to about 74 wt %. In yet other examples, the acidifying component can be included in the inactive NO generating composition in an amount from about 6 wt % to about 87 wt %. In some additional examples, the acidifying component can be included in the inactive NO generating composition in an amount from about 40 wt % to about 60 wt %. In some further examples, the acidifying component can be included in the inactive NO generating composition in an amount from about 60 wt % to about 80 wt %. In still further examples, the acidifying component can be included in the inactive NO generating composition in an amount from about 80 wt % to about 99.5 wt %. Further, the nitrite component and the acidifying component can typically be present in the inactive NO generating composition at a weight ratio of from about 1:30 to about 10:1. In some additional examples, the nitrite component and the acidifying component can be present in the inactive NO generating composition at a weight ratio of from about 1:5 to about 3:1, or from about 1:3 to about 2:1.

As discussed previously, the support material can be used to minimize production of NO upon mixing of the nitrite component and the acidifying agent prior to addition of an activation solvent. Generally, any activation solvent that can provide a suitable reaction environment for the nitrite component and the acidifying agent, that is not toxic, and that does not sequester or bind NO can be used. In some examples, water or other aqueous solvent can act as an activation solvent. As such, in some cases, it can be desirable to maintain low levels of water in the inactive NO generating composition. For example, in some cases, the inactive NO generating composition can include less than about 0.1 wt % water. In other examples, the inactive NO generating composition can include less than about 0.5 wt % water. In yet other examples, the inactive NO generating composition can include less than about 1 wt %, less than 2 wt %, or less than 5 wt % water. In still other examples, the inactive NO generating composition can include less than about 20 wt % water.

In some additional examples, a stable nitric oxide (NO) generating composition can include a blend of a nitrite component and an acidifying agent in a dry, particulate, or powder form. It is noted that the stability of the nitric oxide generating composition can be additionally or alternatively measured in a number of ways. For example, in some cases the stability of the NO generating composition can be measured by accelerated stability testing at room temperature, 40° C., 60° C., or other suitable temperature for a predetermined period of time. Various parameters can be measured at each time point, such as color change, nitric oxide and/or nitrogen dioxide production, the like, or a combination thereof.

In some specific examples, the blend of the nitrite component and the acidifying agent can be sufficiently stable so that after storage for 3 months at room temperature less than 5 part per million (ppm) of NO is detected by chemiluminescence upon opening of the storage container within which the NO generating composition has been stored. In some other examples, less than 1 ppm of NO is detected by chemiluminescence upon opening of the storage container within which the NO generating composition has been stored for 3 months at room temperature. In some further examples, less than 800 parts per billion (ppb), less than 500 ppb, or less than 100 ppb NO can be detected by chemiluminescence upon opening of a storage container within which the NO generating composition has been stored for 3 months at room temperature.

In some additional examples, the blend of the nitrite component and the acidifying agent can be sufficiently stable so that after storage for 6 months, 12 months, or 24 months at room temperature less than 5 ppm of NO is detected by chemiluminescence upon opening of the storage container within which the NO generating composition has been stored. In some other examples, less than 1 ppm of NO is detected by chemiluminescence upon opening of the storage container within which the NO generating composition has been stored for 6 months, 12 months, or 24 months at room temperature. In some further examples, less than 800 ppb, less than 500 ppb, or less than 100 ppb NO can be detected by chemiluminescence upon opening of a storage container within which the NO generating composition has been stored for 6 months, 12 months, or 24 months at room temperature.

In yet additional examples, the blend of the nitrite component and the acidifying agent can be sufficiently stable so that after storage for 6 months at 40° C. less than 5 ppm of NO is detected by chemiluminescence upon opening of the storage container within which the NO generating composition has been stored. In some other examples, less than 1 ppm of NO is detected by chemiluminescence upon opening of the storage container within which the NO generating composition has been stored for 6 months at 40° C. In some further examples, less than 800 ppb, less than 500 ppb, or less than 100 ppb NO can be detected by chemiluminescence upon opening of a storage container within which the NO generating composition has been stored for 6 months at 40° C.

The present disclosure also describes a therapeutic system. The system can include a composition that includes a blend of a nitrite component and an acidifying agent in a dry, particulate, or powder form, such as those described herein, for example. It should be noted, that in some embodiments, the components of a system can all be held together, and in other embodiments, the components of a system can be held separately and the combined or otherwise brought together at a desired time or location in order to provide a specific therapy or effect.

In some examples, the system can also include a container within which the composition is enclosed. The container can have a fill-line visibly marked thereon. A variety of containers can be used. Non-limiting examples can include a bottle, a syringe, a vial, a bucket, a jar, a dish, a pan, a tray, the like, or a combination thereof. The container can include or be made of a variety of materials. Non-limiting examples can include glass, polyethylene, polypropylene, polycarbonate, polyvinyl chloride, the like, or a combination thereof. In some examples, the container can be opaque or amber colored. In other examples, the container can be clear or transparent.

In some examples, the system (e.g. kit) can further include instructions directing a user to fill the container up to the fill-line with an activating solvent, such as an aqueous solvent, to activate the composition. In some examples, the instructions can be disposed on an exterior surface of the container. In other examples the instructions can be separate from the container, but can be included in a shipping package, shipping container, or the like in combination with the container.

In some examples, the system can include a bandage, wrap, cloth, disposable wipe, or other fabric material having the dry composition associated therewith. In such examples, the composition can be activated by applying an activating solvent to the fabric material. In some examples, the fabric material can include a gel layer (e.g. a dehydrated gel layer or other suitable gel layer) that includes the composition. In some further examples, the gel layer can be configured to absorb an activating solvent and activate the composition to produce NO. In some additional examples, the fabric material can include an impermeable backing layer to prevent or minimize NO escape from the fabric material after application of the fabric material to a situs of treatment or other desired surface.

The present disclosure also describes a method of minimizing NO generation prior to activation of a nitric oxide generating composition. The method can include combining an acidifying agent with a support material to form an acidifying component. The method can further include mixing or combining the acidifying component with a nitrite component to form a dry composition having a water content less than 20 wt %, or other suitable water content as described herein. Combining the acidifying agent with the support material can minimize NO generation prior to addition of an activating amount of an activation solvent, such as an aqueous solvent.

Combining the acidifying agent with the support material can be performed in a number of ways. For example, in some cases, the acidifying agent can be encapsulated by the support material. In such cases, the acidifying agent can be physically separated from the nitrite component, which can prevent a chemical reaction between the acidifying agent and the nitrite component to generate NO prior to activation or release of the acidifying agent from the support material. In some other examples, the acidifying agent can be coated onto the support material. This can tie up or encapsulate the acidifying agent on the support material, similarly minimizing or preventing a chemical reaction between the acidifying agent and the nitrite component to generate NO prior to activation or release of the acidifying agent from the support material.

Further, in some cases, the type of encapsulation or immobilization of the acidifying agent on the support material can further affect a rate of reaction between the acidifying agent and the nitrite component upon or after activation. For example, in some cases, addition of an activation solvent, such as an aqueous solvent, can immediately release the acidifying agent from the support material making the acidifying agent immediately available for reaction with the nitrite component. In other examples, the encapsulation or immobilization of the acidifying agent can be such that addition of an activation solvent does not result in immediate release of the acidifying agent. Rather, in some examples, there can be a slightly delayed onset of NO generation due to a delayed release of the acidifying agent from the support material. In still other examples, the activation solvent can be formulated to facilitate either immediate or delated release of the acidifying agent from the support material and/or immediate or delayed solvation of the acidifying agent to generate NO.

The present disclosure also describes a method of making an inactive nitric oxide (NO) generating composition. The method can include combining an acidifying agent with a support material to form an acidifying component. The method can also include mixing or combining the acidifying component with the nitrite component in a dry, particulate, or powder form. Combining the acidifying agent with a support material can minimize NO generation prior to addition of an activating amount of an activation solvent, such as an aqueous solvent.

It is further noted that the inactive NO generating composition can be subsequently activated via the addition of an activating amount of an activation solvent. In further detail, a nitric oxide releasing composition can include an effective amount of an acidifying agent, a nitrite component in an amount sufficient to generate a therapeutically effective amount of nitric oxide (NO) when combined with the effective amount of the acidifying agent, a support material, and an activating amount of an activation solvent, such as an aqueous solvent. At least a portion of the support material can be dissociated from the acidifying agent or the nitrite component.

In some specific examples, the amount of acidifying agent present in the NO releasing composition can affect the rate and amount of NO generated from the NO releasing composition. In some examples, the acidifying agent can be present in the NO releasing composition in an amount from about 0.05 w/v % to about 10 w/v %. In some examples, the amount of acidifying agent is no greater than about 5.0 w/v % of the solution. In other examples, the amount of acidifying agent is about or greater than 0.5 w/v % of the NO generating composition. In another example, the amount of acidifying agent is about or greater than 0.2 w/v % of the NO generating composition. In a further example, the amount of acidifying agent is about or greater than 0.07 w/v % of the NO generating composition. In another example, the amount of acidifying agent is between about 0.07 w/v % and about 5.0 w/v % of the NO generating composition. In another example, the amount of acidifying agent is between about 0.07 w/v % and about 3.0 w/v % of the NO generating composition. In another example, the amount of acidifying agent is between about 5.0 w/v % and about 10.0 w/v % of the NO generating composition.

In some additional examples, the nitrite component of the NO generating composition can be present in the composition in an amount of from about 0.05 w/v % to about 7.0 w/v %. In another example, the concentration of the nitrite component in the composition can be from 0.07 w/v % to about 1.0 w/v %. In another example, the concentration of the nitrite component in the composition can be from about 1.0 w/v % to about 2.0 w/v %. In another example, the concentration of the nitrite component in the composition can be from about 1.0 w/v % to about 1.5 w/v %. In another example, the concentration of the nitrite component in the composition can be from about 1.5 w/v % to about 2.0 w/v %. In one example, the concentration of the nitrite component in the composition is no greater than about 0.5 w/v %. In another example, the concentration of the nitrite component in the composition is from about 0.07 w/v % to about 0.5 w/v %. In a further example, the concentration of the nitrite component in the composition can be from about 0.05 w/v % to about 10 w/v %. In one specific example, when sodium nitrite is used as the nitrite component, the concentration of sodium nitrite can be from about 0.41 w/v % to about 0.69 w/v % in the composition. In another specific example, when sodium nitrite is used as the nitrite component, the concentration of sodium nitrite can be from about 0.3 w/v % to about 3.0 w/v % in the composition. In another specific example, when sodium nitrite is used as the nitrite component, the concentration of sodium nitrite in the composition can be from about 0.3 w/v % to about 1.0% w/v. In another specific example, when sodium nitrite is used as the nitrite component, the concentration of sodium nitrite in the composition can be from about 1.0 w/v % to about 1.5 w/v %. In another specific example, when sodium nitrite is used as the nitrite component, the concentration of sodium nitrite in the composition can be from about 1.5 w/v % to about 2.0 w/v %. In another specific example, when sodium nitrite is used as the nitrite component, the concentration of sodium nitrite in the composition can be from about 2.0 w/v % to about 2.5 w/v %. In another specific example, when sodium nitrite is used as the nitrite component, the concentration of sodium nitrite in the composition can be from about 2.5 w/v % to about 3.0 w/v %.

In an additional example, the amount of nitrite component present in the NO generating composition can be an amount of from about 1 mM to about 1 M. In another example, the amount of nitrite component present in the NO generating composition can be an amount of from about 10 mM to about 500 mM. In another example, the amount of nitrite component present in the NO generating composition can be an amount of from about 50 mM to about 400 mM. In another example, the amount of nitrite component present in the NO generating composition can be an amount of from about 100 mM to about 400 mM. In yet a further example, the amount of nitrite component present in the NO generating composition can be an amount of from about 100 mM to about 200 mM. In another example, the amount of nitrite component present in the NO generating composition can be an amount of from about 200 mM to about 300 mM. In an additional example, the amount of nitrite component present in the NO generating composition can be an amount of from about 300 mM to about 400 mM. In another example, the amount of nitrite component present in the NO generating composition can be an amount of from about 400 mM to about 500 mM. In an additional example, the amount of nitrite component present in the NO generating composition can be an amount of from about 40 mM to about 180 mM. In an additional example, the amount of nitrite component present in the NO generating composition can be an amount of from about 40 mM to about 120 mM.

In some further examples, one of the acidifying agent and the nitrite component is present in the NO generating composition in an amount greater than 0.5 w/v %. In some examples, the acidifying agent is present in the NO generating composition in an amount greater than 0.5 w/v %. In other examples, the nitrite component is present in the NO generating composition in an amount greater than 0.5 w/v %.

The support material can be present in the NO generating composition in a variety of different forms, depending on the particular NO generating composition. In some examples, a portion of the support material can be physically, chemically, or otherwise associated with the nitrite component, the acidifying agent, or both. In some examples, a portion of the support material can be dissociated from the nitrite component, the acidifying agent, or both. In some examples, when the support material becomes dissociated from the nitrite component, the dissociated support material can form a precipitate or other undissolved component that can settle at the bottom of the NO generating composition. In other examples, the dissociated support material can form a film that can adhere to walls of a container, float on a surface of the NO generating composition, the like, or a combination thereof. In some examples, the support material can be dissolved in the activation solvent. In some other examples, the support material can be suspended or dispersed in the activation solvent.

It is noted that the nitric oxide releasing composition can include an activating amount of an activation solvent to convert an inactive NO generating composition to an active form. By "active," it is meant that the composition is in a state and/or form that readily produces nitric oxide. In some examples, the amount of activation solvent can depend on a particular application of the NO releasing composition. As described above, any suitable activation solvent can be used that can provide a suitable reaction environment for the nitrite component and the acidifying agent, that is not toxic, and that does not otherwise excessively sequester or bind the NO generated by the NO generating composition. Non-limiting examples of activation solvents can include aqueous activation solvents (e.g. water, saline solutions, etc.), body fluids (e.g. wound exudates, blood, urine, sweat, saliva, etc.), non-aqueous hydrophilic solvents (e.g. ethanol, glycerin, propylene glycol, etc.), the like, or a combination thereof.

The NO releasing composition can be formulated in a number of ways. In some examples, the NO releasing composition can be formulated as a solution. In other examples, the NO releasing composition can be formulated as a gel. Where the NO releasing composition is formulated as a gel, the NO releasing composition can include a variety of gelling agents, such as those listed elsewhere herein, or other suitable gelling agent.

The NO releasing composition can be used to treat a number of adverse health conditions (e.g. conditions responsive to NO therapy). Such methods of treatment can include topically administering a nitric oxide releasing composition as described herein to a treatment situs of a subject. In some examples, the nitric oxide releasing composition can be topically administered to a treatment situs as an inactive NO generating composition and subsequently activated via the addition of an activating amount of an activation solvent. In some other examples, the nitric oxide releasing composition can be topically administered as an already activated composition. However, in some examples, it can be desirable to activate the NO releasing composition within about 60 minutes of topical administration. In yet other examples, it can be desirable to activate the NO releasing composition within about 30 minutes, 20 minutes, 10 minutes, or 5 minutes of topical administration.

The NO releasing composition can be used to treat a variety of adverse health conditions. Generally, any topical infection can be treated with the NO releasing composition. Some specific, but non-limiting, examples of conditions that can be treated with the NO releasing compositions can include athlete's foot, onychomycosis, sinusitis, pharyngitis, a cold virus, influenza, acne, atopical dermatitis, wounds, diabetic foot ulcer, otitis externa, the like, or a combination thereof.

Depending on the particular condition being treated, the NO releasing composition can be topically administered by immersing, wiping, soaking, covering, flooding, flushing, wetting, spraying, or otherwise contacting the treatment situs with the NO releasing composition, or other suitable application method, or a combination thereof. For example, in some cases, the NO releasing composition can be used as a foot bath, or the like, for immersing a treatment situs in the NO releasing composition. In some examples, the NO releasing composition can be sprayed into a nasal canal, onto the skin, or the like, to treat an adverse health condition at a situs of treatment. In other examples, the NO releasing composition can be applied to or form a part of a bandage or other fabric material for covering, soaking, wiping, etc. the treatment situs with the NO releasing composition. In still other examples, the NO releasing composition can be formulated or applied as drops into the outer ear, for rinsing open or closed wounds, or the like. A variety of other application methods can also be employed.

The NO releasing composition can also be used to sanitize a hard surface. This can be done by applying a nitric oxide releasing composition as described herein to a hard surface. Again, application can be performed by immersing, wiping, soaking, spraying, covering, etc. the hard surface with the NO releasing composition. This method can be performed with any suitable hard surface. Non-limiting examples can include a countertop, a floor, a sink, a toilet, a bathtub, a shower, a doorknob, a scientific instrument, a medical instrument, the like, or a combination thereof.

EXAMPLES

Certain invention embodiments are further described in detail by reference to the following experimental example. This example is provided for purposes of illustration only, and is not intended to be limiting unless otherwise specified. Thus, the invention should in no way be construed as being limited to the following example, but rather, should be construed to encompass any and all variations which become evident as a result of the teaching provided herein.

Example 1: Stability and Antimicrobial Activity of Various Nitric Oxide Releasing Compositions 20 mM NORS (50 mL), using coated citric acid, was made by mixing 20 mM sodium nitrite solution and the coated citric acid with a net weight of 0.07 g (see Table 1 for gross weight). A control of 20 mM NORS, using uncoated citric acid, was used. The pH of each NORS was measured using an Orion Star A211 pH meter and NO and $NO_2$ production was measured using a PulmoNOx detector.

TABLE 1

List of samples, their coating, percent citric acid, amount added to make 20 mM NORS and amount added with 7.0 g of sodium nitrite.

| Code | Carrier name | % Citric Acid | Amount Added to make 20 mM NORS | Amount Added to 7.0 g of $NaNO_2$ | Volume of $NaNO_2$ + Citric Acid |
|---|---|---|---|---|---|
| 6A | Sipernat 2200 | 57.2% | 0.122 g | 12.24 g | 30 mL |
| 6B | Sipernat 2200 | 66.0% | 0.106 g | 10.61 g | 27.5 mL |
| 6C | Sipernat 2200 | 57.8% | 0.121 g | 12.11 g | 32.5 mL |
| 7A | Sipernat 50 | 78.7% | 0.089 g | 8.89 g | 15 mL |
| 7B | Sipernat 50 | 82.6% | 0.083 g | 8.33 g | 17.5 mL |
| 8A | Sipernat 500LS | 76.3% | 0.092 g | 9.17 g | 20 mL |
| 8B | Sipernat 500LS | 83.0% | 0.084 g | 8.43 g | 17.5 mL |
| 9A | Zeofree 5161 | 64.0% | 0.109 g | 10.94 g | 27.5 mL |
| 9B | Zeofree 5161 | 71.0% | 0.099 g | 9.86 g | 25 mL |
| 9C | Zeofree 5161 | 63.8% | 0.110 g | 10.97 g | 22.5 mL |
| 10A | Zeofree 5162 | 65.3% | 0.107 g | 10.72 g | 25 mL |
| 10B | Zeofree 5162 | 71.0% | 0.099 g | 9.86 g | 20 mL |
| 10C | Zeofree 5162 | 62.4% | 0.112 g | 11.22 g | 25 mL |
| 11A | Hubersorb 600 | 71.7% | 0.098 g | 9.76 g | 15 mL |
| 11B | Hubersorb 600 | 75.0% | 0.093 g | 9.33 g | 15 mL |
| 12 | Aerosil R812 | 95.0% | 0.074 g | 7.37 g | 12.5 mL |
| 13 | Aerosil R972 | 95.0% | 0.074 g | 7.37 g | 12.5 mL |
| 14 | Aerosil R972 | 99.5% | 0.0704 g | 7.035 g | 12.5 mL |
| 15 | Aerosil R972 | 99.0% | 0.0707 g | 7.070 g | 12.5 mL |
| 16 | Aerosil R972 | 98.0% | 0.0714 g | 7.143 g | 12.5 mL |
| 17 | Aerosil R972 | 97.0% | 0.0722 g | 7.216 g | 12.5 mL |
| 18 | Sipernat 50 | 72.9% | 0.0960 g | 9.602 g | |
| 19 | Sipernat 50 | 80.8% | 0.0866 g | 8.663 g | |

All samples included undissolved material (e.g. solid material settling at the bottom of the container, film building up on the walls of the container and/or top of fluid, etc.) which began to appear within about a minute after mixing. In samples 11A and 11B (hubersorb coating) the pH measured was higher than normal, at 3.81 and 3.74 respectively. For the others the pH, NO and $NO_2$ was found to be similar to the control (Table 2). Samples 6A, 6B, 7A, 7B, 10A, 10B, 10C tended to have lower $NO_2$ release. In contrast, samples 9A, 9B, and 9C after mixing with sodium nitrite had higher $NO_2$ than the control.

TABLE 2

A comparison with the 20 mM NORS with silica coverings with a control. pH was measured using the Orion Star A211 pH meter and NO and $NO_2$ was measured using the PulmoNOx.

| Sample | pH | NO (ppm) | $NO_2$ (ppm) |
|---|---|---|---|
| Control | 3.56 | 3 | 5.6 |
| 6A | 3.56 | 2 | 3.6 |
| 6B | 3.53 | 3 | 3.2 |
| 6C | 3.55 | 1 | 5.3 |
| 7A | 3.53 | 2 | 3.4 |
| 7B | 3.53 | 2 | 3.5 |
| 8A | 3.55 | 2 | 5.2 |
| 8B | 3.53 | 3 | 5.7 |
| 9A | 3.55 | 1 | 6.4 |
| 9B | 3.55 | 2 | 6.3 |
| 9C | 3.55 | 1 | 6.9 |
| 10A | 3.55 | 3 | 2.9 |
| 10B | 3.55 | 2 | 2.3 |
| 10C | 3.57 | 2 | 2.6 |
| 11A | 3.81 | 2 | 1.9 |
| 11B | 3.74 | 1 | 2.2 |
| 12 | 3.58 | 0 | 0.6 |
| 13 | 3.58 | 0 | 1.2 |
| Control | 3.56 | 3 | 2.8 |
| 14 | 3.57 | 2 | 2.3 |
| 15 | 3.57 | 2 | 2.0 |
| 16 | 3.58 | 1 | 1.7 |
| 17 | 3.58 | 1 | 1.5 |
| 18 | 3.56 | 2 | 1.9 |
| 19 | 3.56 | 2 | 2.1 |

Stability

The stability of each composition was measured by mixing 7.0 g of sodium nitrite with a net weight of 7.0 g of the coated citric acid (see Table 1 for gross weight). A control of 7.0 g of sodium nitrite and 7.0 g of citric acid was used. NO and $NO_2$ was measured over 2 days using an electrochemical NO/NO2 analyzer (PulmoNOx IIa, Tofield, Canada).

NO and $NO_2$ generally were not detected in the samples after 24 and 48 hours of mix, except in samples 8A and 6A. (See Table 3).

TABLE 3

Stability of dry sodium nitrite (7 g) mixed with citric acid (7 g, net weight).
NO and $NO_2$ was measured using the PulmoNOx.

| Sample | 0 hours NO (ppm) | 0 hours $NO_2$ (ppm) | 24 hours NO (ppm) | 24 hours $NO_2$ (ppm) | 48 hours NO (ppm) | 48 hours $NO_2$ (ppm) | 1 month NO (ppm) | 1 month $NO_2$ (ppm) |
|---|---|---|---|---|---|---|---|---|
| Control | 200 | 15.6 | 22 | 12.5 | 8 | 5.8 | | |
| 6A | 0 | 0 | 107 | >21.5 | 48 | 6.7 | 0 | 0.4 |
| 6B | 0 | 0 | 0 | 0 | 0 | 0 | 0 | 0 |
| 6C | 0 | 0 | 0 | 0 | 0 | 0 | 0 | 0 |
| 7A | 0 | 0 | 0 | 0 | 0 | 0 | 0 | 0 |
| 7B | 0 | 0 | 0 | 0 | 0 | 0 | 0 | 0 |
| 8A | 203 | >21.5 | 66 | >21.5 | 11 | >21.5 | 0 | 0.4 |
| 8B | 0 | 0 | 0 | 0 | 0 | 0 | 0 | 0 |
| 9A | 0 | 0 | 0 | 0 | 0 | 0 | 0 | 0.1 |
| 9B | 0 | 0 | 0 | 0 | 0 | 0 | 0 | 0 |
| 9C | 0 | 0 | 0 | 0 | 0 | 0 | 0 | 0 |
| 10A | 0 | 0 | 0 | 0 | 0 | 0 | 0 | 0 |
| 10B | 0 | 0 | 0 | 0 | 0 | 0 | 0 | 0 |
| 10C | 0 | 0 | 0 | 0 | 0 | 0 | 0 | 0 |
| 11A | 0 | 0 | 0 | 0 | 0 | 0 | 0 | 0 |
| 11B | 0 | 0 | 0 | 0 | 0 | 0 | 0 | 0 |
| 12 | 0 | 0 | 0 | 0 | 0 | 0 | 0* | 0* |
| 13 | 0 | 0 | 0 | 0 | 0 | 0 | 0* | 0* |
| 14 | 0 | 0 | 0 | 0 | 0 | 0 | 532 | >21.5 |
| 15 | 0 | 0 | 0 | 0 | 0 | 0 | 346 | >21.5 |
| 16 | 0 | 0 | 0 | 0 | 0 | 0 | 336 | >21.5 |
| 17 | 0 | 0 | 0 | 0 | 0 | 0 | 0 | 0 |
| 18 | 0 | 0 | 0 | 0 | 0 | 0 | 0 | 0 |
| 19 | 0 | 0 | 0 | 0 | 0 | 0 | 0 | 0 |

*Samples 12 and 13 were measured 1 week later.

Antimicrobial Properties

Antimicrobial properties were tested using 20 mM NORS solutions, as described above. 990 µL of NORS was placed into a centrifuge tube. Saline was used as a control. 10 µL of $10^8$ CFU/mL of *Salmonella typhi* was added to the tube resulting in a final concentration of $10^6$ CFU/mL. Exposure times of 2 and 5 minutes were used. The bacteria were plated onto BHI plates and incubated at 37° C. overnight.

The coated NORS retained its antimicrobial properties against *S. typhi* in all the samples. In general, 2 minutes post treatment an average of $10^2$ was found, by 5 minutes no detectable bacteria was found. The treatments that were using samples 7A, 11A, and 11B had a higher bacterial concentration after 2 minutes (possibly due to the higher pH found after mixing the NORS in the 11 samples) but still had complete eradication after 5 min.

TABLE 4

Antimicrobial effect of 20 mM NORS with silica covering.
No detectable bacteria was found after 5 minutes.

| Sample | Control | 2 min (CFU/mL) | 5 min (CFU/mL) |
|---|---|---|---|
| 6A | 1.13*$10^6$ | 2.0*$10^2$ | 0 |
| 6B | 1.13*$10^6$ | 6.0*$10^1$ | 0 |
| 6C | 1.13*$10^6$ | 5.0*$10^1$ | 0 |
| 7A | 1.13*$10^6$ | 5.8*$10^3$ | 0 |
| 7B | 1.13*$10^6$ | 3.0*$10^1$ | 0 |
| 8A | 1.13*$10^6$ | 4.0*$10^2$ | 0 |
| 8B | 1.13*$10^6$ | 4.0*$10^1$ | 0 |
| 9A | 1.13*$10^6$ | 2.0*$10^1$ | 0 |
| 9B | 1.13*$10^6$ | 7.0*$10^1$ | 0 |
| 9C | 1.13*$10^6$ | 2.0*$10^2$ | 0 |
| 10A | 1.13*$10^6$ | 3.0*$10^2$ | 0 |
| 10B | 1.13*$10^6$ | 2.0*$10^2$ | 0 |
| 10C | 1.13*$10^6$ | 4.0*$10^2$ | 0 |
| 11A | 1.13*$10^6$ | 3.0*$10^5$ | 0 |
| 11B | 1.13*$10^6$ | 6.0*$10^4$ | 0 |
| 12 | 8.9*$10^5$ | 2.0*$10^2$ | 0 |
| 13 | 8.9*$10^5$ | 4.3*$10^2$ | 0 |
| 14 | 2.6*$10^6$ | 4.8*$10^2$ | 0 |
| 15 | 2.6*$10^6$ | 7.0*$10^1$ | 0 |
| 16 | 2.6*$10^6$ | 1.3*$10^2$ | 0 |
| 17 | 2.6*$10^6$ | 2.0*$10^2$ | 0 |
| 18 | 2.6*$10^6$ | 0 | 0 |
| 19 | 2.6*$10^6$ | 2.0*$10^2$ | 0 |

TABLE 5

Antimicrobial effect of 20 mM NORS with silica covering against
*S. aureus* and *E. coli*. No detectable bacteria was found after 10 minutes.

| | *S. aureus* | | | *E. coli* | | |
|---|---|---|---|---|---|---|
| Sample | Control | 5 min (CFU/mL) | 10 min (CFU/mL) | Control | 5 min (CFU/mL) | 10 min (CFU/mL) |
| control | 1.20*$10^6$ | 1.7*$10^3$ | 0 | 2.40*$10^6$ | 2*$10^2$ | 0 |
| 7A | 1.20*$10^6$ | 3.5*$10^3$ | 0 | 2.40*$10^6$ | 2.0*$10^2$ | 0 |
| 7B | 1.20*$10^6$ | 4.2*$10^3$ | 0 | 2.40*$10^6$ | 8.0*$10^1$ | 0 |
| 12 | 1.20*$10^6$ | 2.1*$10^3$ | 0 | 2.40*$10^6$ | 1.4*$10^2$ | 0 |
| 13 | 1.20*$10^6$ | 4.5*$10^3$ | 0 | 2.40*$10^6$ | 1.2*$10^2$ | 0 |

Example Embodiments

In one example, there is provided a particulate composition, comprising a blend of a nitrite component and an acidifying agent, wherein one, but not both, of the nitrite component and the acidifying agent is carried by a support material.

In one example of a particulate composition, the nitrite component comprises sodium nitrite, potassium nitrite, barium nitrite, calcium nitrite, nitrite orotate, amyl nitrite, magnesium nitrite, or a combination thereof.

In one example of a particulate composition, the acidifying agent comprises ascorbic acid, ascorbyl palmitate, salicylic acid, malic acid, lactic acid, citric acid, formic acid, benzoic acid, tartaric acid, hydrochloric acid, sulfuric acid, phosphoric acid, or a combination thereof.

In one example of a particulate composition, the support material comprises carbon black, activated carbon, a metal oxide, a silica, a silicate, a metal phosphate, or a combination thereof.

In one example of a particulate composition, the support material has a surface area of at least 0.1 meters squared per gram ($m^2/g$).

In one example of a particulate composition, the support material has a pore volume of at least 0.01 cubic centimeters per gram (cc/g).

In one example of a particulate composition, the support material is a calcined support material.

In one example of a particulate composition, the nitrite component and the acidifying agent are present in the particulate composition at a weight ratio of from about 1:2 to about 2:1.

In one example of a particulate composition, the support material can be present in the particulate composition at a weight ratio of from about 0.05:1 to about 10:1 with the nitrite component or the acidifying agent.

In one example of a particulate composition, the nitrite component is present in the particulate composition in an amount of from about 0.05 wt % to about 99.5 wt %.

In one example of a particulate composition, the acidifying agent is present in the particulate composition in an amount of from about 0.05 wt % to about 99.5 wt %.

In one example of a particulate composition, the support material is present in the particulate composition in an amount of from about 0.05 wt % to about 99.5 wt %.

In one example of a particulate composition, the nitrite component is carried by the support material.

In one example of a particulate composition, the acidifying agent is carried by the support material.

In one example, there is provided an inactive nitric oxide (NO) generating composition, comprising a nitrite component; and an acidifying component, said acidifying component comprising an acidifying agent carried by a support material, wherein the nitrite component and the acidifying component are mixed together in a dry form.

In one example of an inactive nitric oxide (NO) generating composition, the nitrite component comprises sodium nitrite, potassium nitrite, barium nitrite, calcium nitrite, nitrite orotate, amyl nitrite, magnesium nitrite, or a combination thereof.

In one example of an inactive nitric oxide (NO) generating composition, the nitrite component is present in the composition in an amount of from about 0.05 wt % to about 99.5 wt %.

In one example of an inactive nitric oxide (NO) generating composition, the acidifying agent comprises ascorbic acid, ascorbyl palmitate, salicylic acid, malic acid, lactic acid, citric acid, formic acid, benzoic acid, tartaric acid, hydrochloric acid, sulfuric acid, phosphoric acid, or a combination thereof.

In one example of an inactive nitric oxide (NO) generating composition, the acidifying component is present in the composition in an amount of from about 0.05 wt % to about 99.5 wt %.

In one example of an inactive nitric oxide (NO) generating composition, the support material comprises carbon black, activated carbon, a metal oxide, a silica, a silicate, a metal phosphate, or a combination thereof.

In one example of an inactive nitric oxide (NO) generating composition, the support material has a surface area of at least 0.1 meters squared per gram ($m^2/g$).

In one example of an inactive nitric oxide (NO) generating composition, the support material has a pore volume of at least 0.01 cubic centimeters per gram (cc/g).

In one example of an inactive nitric oxide (NO) generating composition, the support material is a calcined support material.

In one example of an inactive nitric oxide (NO) generating composition, the support material and the acidifying agent are present at a weight ratio of from about 0.05:1 to about 10:1.

In one example of an inactive nitric oxide (NO) generating composition, the composition includes less than 20 wt % water.

In one example there is provided a stable nitric oxide (NO) generating composition, comprising a blend of a nitrite component and an acidifying agent in a dry form, wherein less than 1 part per million (ppm) of nitric oxide is detectable by chemiluminescence upon opening a storage container within which the blend has been stored for 3 months at room temperature.

In one example of a stable nitric oxide (NO) generating composition, the nitrite component comprises sodium nitrite, potassium nitrite, barium nitrite, calcium nitrite, nitrite orotate, amyl nitrite, magnesium nitrite, or a combination thereof.

In one example of a stable nitric oxide (NO) generating composition, the nitrite component is present in the composition in an amount of from about 0.05 wt % to about 99.5 wt %.

In one example of a stable nitric oxide (NO) generating composition, the acidifying agent comprises ascorbic acid, ascorbyl palmitate, salicylic acid, malic acid, lactic acid, citric acid, formic acid, benzoic acid, tartaric acid, hydrochloric acid, sulfuric acid, phosphoric acid, or a combination thereof.

In one example of a stable nitric oxide (NO) generating composition, the acidifying agent is present in the composition in an amount of from about 0.05 wt % to about 99.5 wt %.

In one example of a stable nitric oxide (NO) generating composition, the composition includes less than 20 wt % water.

In one example of a stable nitric oxide (NO) generating composition, the composition further comprises a support material configured to carry the nitrite component or the acidifying agent and minimize generation of NO prior to activation.

In one example of a stable nitric oxide (NO) generating composition, the support material comprises carbon black, activated carbon, a metal oxide, a silica, a silicate, a metal phosphate, or a combination thereof.

In one example, there is provided a therapeutic system, comprising a composition comprising a blend of a nitrite component and an acidifying agent in a dry form, wherein one, but not both, of the nitrite component and the acidifying agent is carried by a support material; a container within which the composition is enclosed, said container having a fill-line; and instructions directing a user to fill the container up to the fill-line with an activation solvent to activate the composition.

In one example of a a therapeutic system, the nitrite component comprises sodium nitrite, potassium nitrite, barium nitrite, calcium nitrite, nitrite orotate, amyl nitrite, magnesium nitrite, or a combination thereof.

In one example of a a therapeutic system, the acidifying agent comprises ascorbic acid, ascorbyl palmitate, salicylic acid, malic acid, lactic acid, citric acid, formic acid, benzoic acid, tartaric acid, hydrochloric acid, sulfuric acid, phosphoric acid, or a combination thereof.

In one example of a a therapeutic system, the support material comprises carbon black, activated carbon, a metal oxide, a silica, a silicate, a metal phosphate, or a combination thereof.

In one example of a a therapeutic system, the nitrite component is carried by the support material.

In one example of a a therapeutic system, the acidifying agent is carried by the support material.

In one example of a a therapeutic system, the container comprises one or more of glass, polyethylene, polypropylene, polycarbonate, and polyvinyl chloride.

In one example, there is provided a method of minimizing NO generation prior to activation of a nitric oxide generating composition, comprising combining an acidifying agent with a support material to form an acidifying component; mixing the acidifying component with a nitrite component to form a dry composition having a water content less than 5 wt %, wherein combining the acidifying agent with a support material minimizes NO generation prior to addition of an activating amount of an aqueous solvent.

In one example of a method of minimizing NO generation prior to activation of a nitric oxide generating composition, combining comprises coating the acidifying agent onto the support material.

In one example of a method of minimizing NO generation prior to activation of a nitric oxide generating composition, combining comprises encapsulating the acidifying agent within the support material.

In one example, there is provided a method of making an inactive nitric oxide (NO) generating composition, comprising combining an acidifying agent with a support material to form an acidifying component; mixing the acidifying component with a nitrite component in dry form, wherein combining the acidifying agent with a support material minimizes NO generation prior to addition of an activating amount of an aqueous solvent.

In one example of a method of making an inactive nitric oxide (NO) generating composition, combining comprises coating the acidifying agent onto the support material.

In one example of a method of making an inactive nitric oxide (NO) generating composition, combining comprises encapsulating the acidifying agent within the support material.

In one example there is provided a nitric oxide releasing composition, comprising an effective amount of an acidifying agent; a nitrite component in an amount sufficient to generate a therapeutically effective amount of nitric oxide (NO) when combined with the effective amount of the acidifying agent; a support material, wherein at least a portion of the support material is dissociated from the acidifying agent or the nitrite component; and an activating amount of an activation solvent.

In one example of a nitric oxide releasing composition, the acidifying agent comprises ascorbic acid, ascorbyl palmitate, salicylic acid, malic acid, lactic acid, citric acid, formic acid, benzoic acid, tartaric acid, hydrochloric acid, sulfuric acid, phosphoric acid, or a combination thereof.

In one example of a nitric oxide releasing composition, the acidifying agent is present in the composition in an amount of from about 0.07 w/v % to about 10.0 w/v %.

In one example of a nitric oxide releasing composition, the nitrite component is present in the composition in an amount of from about 0.07 w/v % to about 10.0 w/v %.

In one example of a nitric oxide releasing composition, one of the acidifying agent and the nitrite component is present in an amount greater than 0.5 w/v %.

In one example of a nitric oxide releasing composition, the nitrite component comprises sodium nitrite, potassium nitrite, barium nitrite, calcium nitrite, nitrite orotate, amyl nitrite, magnesium nitrite, or a combination thereof.

In one example of a nitric oxide releasing composition, the support material and the acidifying agent are present at a weight ratio of from about 0.05:1 to about 10:1.

In one example of a nitric oxide releasing composition, the composition is formulated as a solution.

In one example of a nitric oxide releasing composition, the support material comprises carbon black, activated carbon, a metal oxide, a silica, a silicate, a metal phosphate, or a combination thereof.

In one example, there is provided a method of treating an adverse health condition, (e.g. a condition responsive to NO therapy or administration), comprising topically administering a nitric oxide releasing composition as recited herein to a treatment situs of a subject.

In one example of a method of treating an adverse health condition, the adverse health condition comprises athlete's foot, onychomycosis, sinusitis, pharyngitis, a cold virus, influenza, acne, atopical dermatitis, wounds, diabetic foot ulcer, or a combination thereof.

In one example of a method of treating an adverse health condition, topically administering includes immersing, wiping, soaking, covering, or spraying the treatment situs with the nitric oxide releasing composition, or a combination thereof.

In one example of a method of treating an adverse health condition, topically administering includes applying the nitric oxide releasing composition to a fabric material and applying the fabric material to the treatment situs.

In one example of a method of treating an adverse health condition, the treatment situs includes a nasal canal, a skin surface, or a combination thereof.

In one example, there is provided a method of sanitizing a hard surface, comprising applying a nitric oxide releasing composition as recited herein to a hard surface.

In one example of a method of sanitizing a hard surface, the hard surface is a countertop, a floor, a sink, a toilet, a bathtub, a shower, a doorknob, a scientific instrument, a medical instrument, or a combination thereof.

While these invention embodiments and examples have been with reference particularity, it is apparent that other embodiments and variations of those provided may be devised by others skilled in the art without departing from the spirit and scope of this disclosure. The appended claims are intended to be construed to include all such embodiments and equivalent variations.

What is claimed is:

1. A particulate composition, comprising: a blend of a nitrite component and an acidifying agent, wherein the acidifying agent is carried by a calcined support material, and the nitrite component is not carried by a support material.

2. The particulate composition of claim 1, wherein the nitrite component comprises sodium nitrite, potassium nitrite, barium nitrite, calcium nitrite, nitrite orotate, amyl nitrite, magnesium nitrite, or a combination thereof.

3. The particulate composition of claim 1, wherein the acidifying agent comprises ascorbic acid, ascorbyl palmitate, salicylic acid, malic acid, lactic acid, citric acid, formic acid, benzoic acid, tartaric acid, hydrochloric acid, sulfuric acid, phosphoric acid, or a combination thereof.

4. The particulate composition of claim 1, wherein the support material comprises carbon black, activated carbon, a metal oxide, a silica, a silicate, a metal phosphate, or a combination thereof.

5. The particulate composition of claim 1, wherein the support material has a surface area of at least 0.1 meters squared per gram ($m^2/g$).

6. The particulate composition of claim 1, wherein the support material has a pore volume of at least 0.01 cubic centimeters per gram (cc/g).

7. The particulate composition of claim 1, wherein the nitrite component and the acidifying agent are present in the particulate composition at a weight ratio of from about 1:2 to about 2:1.

8. The particulate composition of claim 1, wherein the support material is present in the particulate composition at a weight ratio of from about 0.05:1 to about 10:1 with the nitrite component or the acidifying agent.

9. The particulate composition of claim 1, wherein the nitrite component is present in the particulate composition in an amount of from about 0.05 wt % to about 99.5 wt %.

10. The particulate composition of claim 1, wherein the acidifying agent is present in the particulate composition in an amount of from about 0.05 wt % to about 99.5 wt %.

11. The particulate composition of claim 1, wherein the support material is present in the particulate composition in an amount of from about 0.05 wt % to about 99.5 wt %.

\* \* \* \* \*